(12) United States Patent
Kabbani

(10) Patent No.: US 9,119,689 B2
(45) Date of Patent: Sep. 1, 2015

(54) MANIPULATOR TOOL FOR LOW-PROFILE BRACKET

(71) Applicant: World Class Technology Corporation, McMinnville, OR (US)

(72) Inventor: Robert Kabbani, Abu Dhabi (AE)

( * ) Notice: Subject to any disclaimer, the term of this patent is extended or adjusted under 35 U.S.C. 154(b) by 83 days.

(21) Appl. No.: 13/860,375

(22) Filed: Apr. 10, 2013

(65) Prior Publication Data

US 2013/0230817 A1    Sep. 5, 2013

Related U.S. Application Data

(63) Continuation-in-part of application No. 13/568,594, filed on Aug. 7, 2012, now Pat. No. 8,807,995.

(51) Int. Cl.
| | |
|---|---|
| *A61C 3/00* | (2006.01) |
| *A61C 7/02* | (2006.01) |
| *A61C 7/30* | (2006.01) |
| *A61C 7/14* | (2006.01) |
| *A61C 7/12* | (2006.01) |

(52) U.S. Cl.
CPC . *A61C 7/023* (2013.01); *A61C 7/02* (2013.01); *A61C 7/14* (2013.01); *A61C 7/146* (2013.01); *A61C 7/30* (2013.01); *A61C 7/12* (2013.01); *A61C 7/141* (2013.01); *A61C 7/303* (2013.01)

(58) Field of Classification Search
CPC ............ A61C 7/12; A61C 7/14; A61C 7/141; A61C 7/143
USPC .............. 433/3–5, 153, 157, 159, 162; 81/46, 81/3.55, 3.7, 3.4, 3.57; 254/199, 243, 25, 254/21, 28, 24, 26 R; 7/166, 161; 227/63
See application file for complete search history.

(56) References Cited

U.S. PATENT DOCUMENTS

| | | | | |
|---|---|---|---|---|
| 2,680,003 | A * | 6/1954 | Feinstein | 254/131 |
| 4,904,183 | A * | 2/1990 | Hannan et al. | 433/3 |
| 7,753,342 | B1 * | 7/2010 | Nolle | 254/25 |
| 2004/0048221 | A1 * | 3/2004 | Jabri | 433/2 |

* cited by examiner

*Primary Examiner* — Yogesh Patel
(74) *Attorney, Agent, or Firm* — Chernoff, Vilhauer, McClung & Stenzel, LLP

(57) ABSTRACT

A tool for insertion and removal of an archwire into low-profile orthodontic brackets includes a handle section and at least one end section having a pair of claws separated by a gap. Each of the pair of claws has a pair of lobes with internal pathways for accommodating an archwire. This enables the archwire to be alternately pushed into and pulled away from an orthodontic bracket.

4 Claims, 10 Drawing Sheets

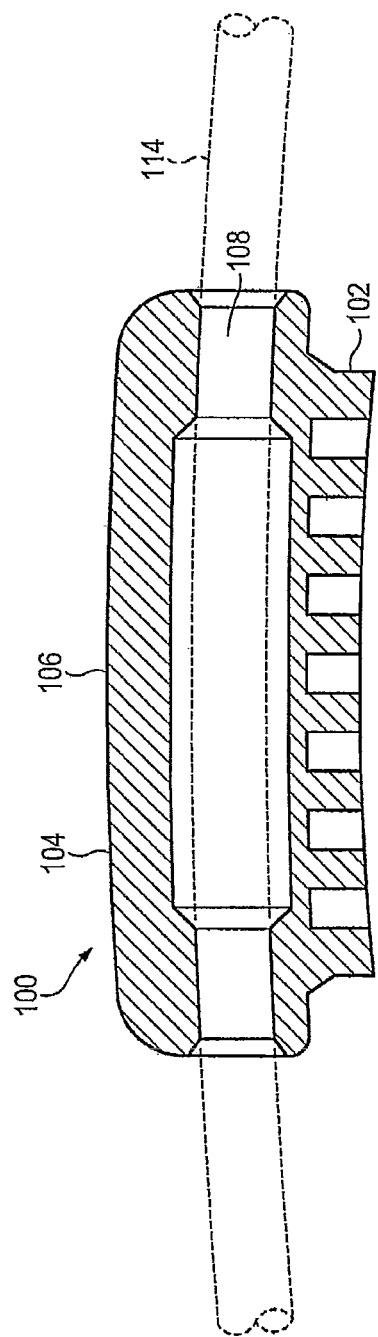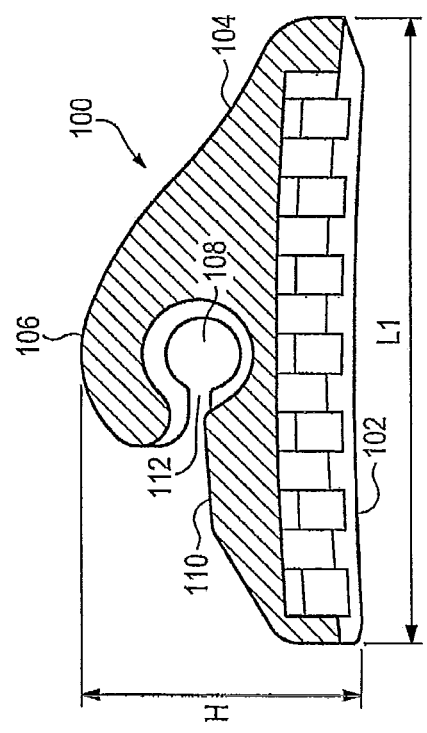

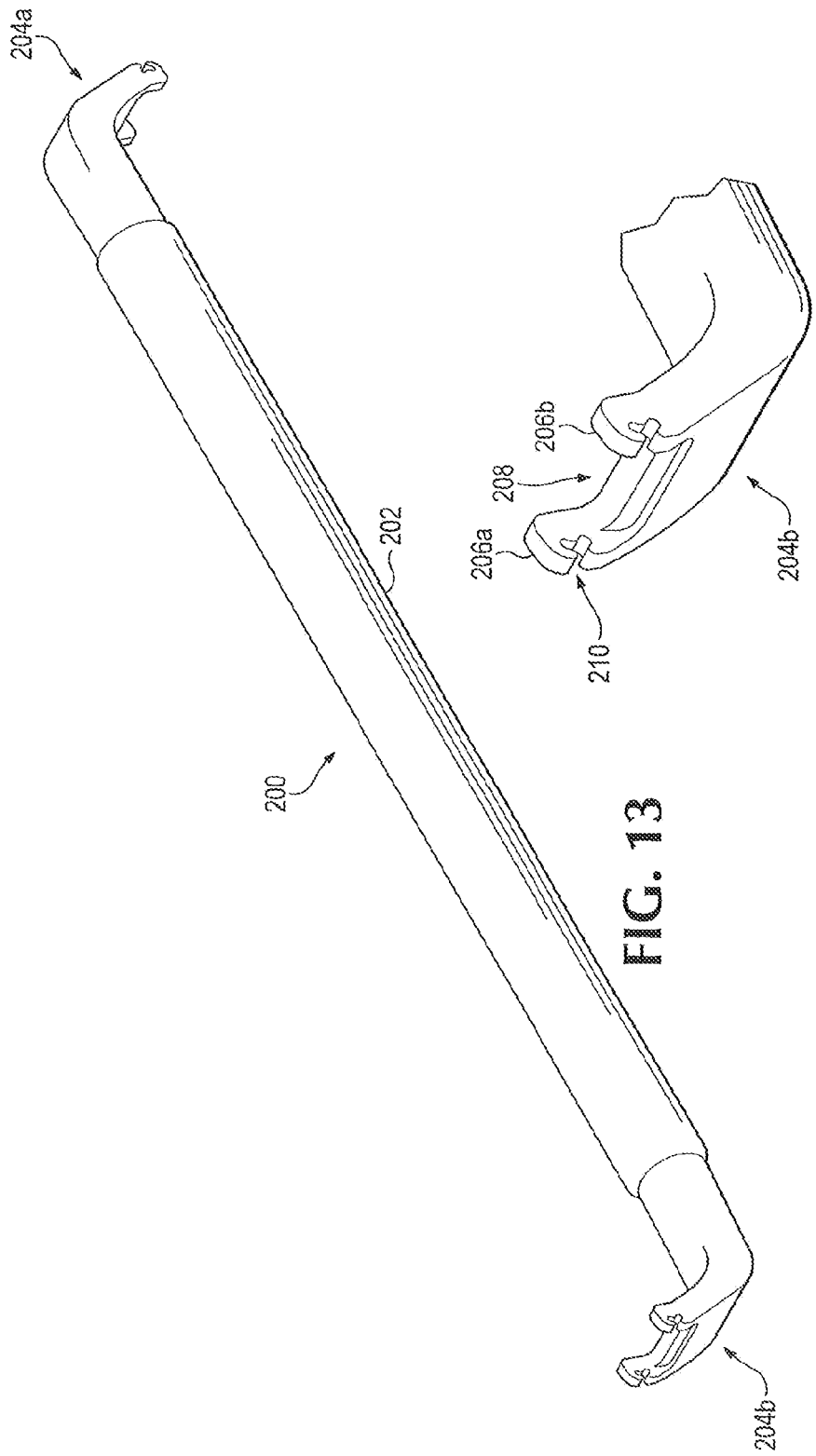

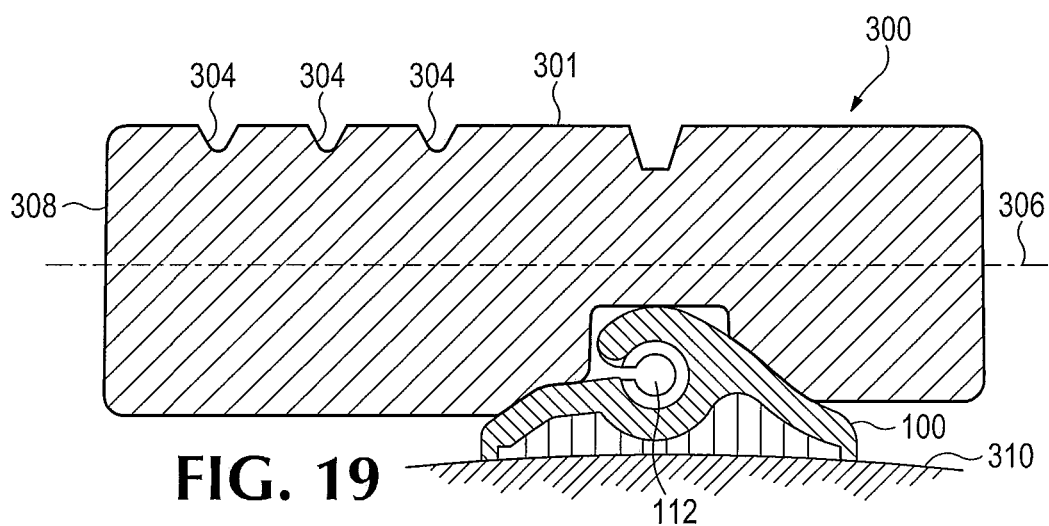
FIG. 19
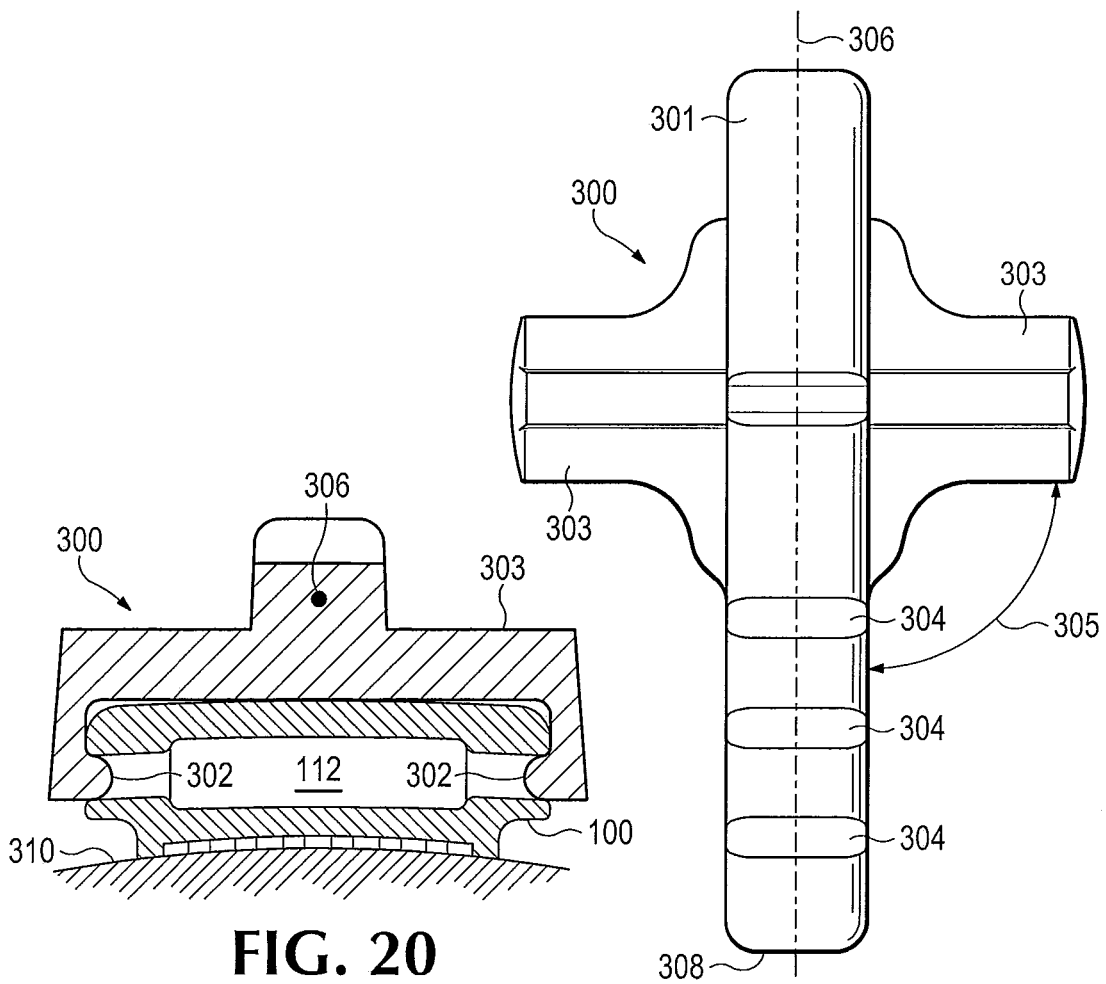
FIG. 20
FIG. 21

MANIPULATOR TOOL FOR LOW-PROFILE BRACKET

CROSS-REFERENCE TO RELATED APPLICATIONS

This application is a continuation-in-part of pending U.S. patent application Ser. No. 13/568,594 filed Aug. 7, 2012, which is a continuation-in-part of pending patent application no. PCT/US2011/024067 filed Feb. 8, 2011, and is related to and claims priority from pending German application DE 10 2010 008 749 filed Feb. 20, 2010.

BACKGROUND OF THE INVENTION

1. Field of the Invention

This invention relates to orthodontic appliances and in particular to orthodontic brackets having a low profile between the top of the tooth and the inner lips so as to minimize irritation.

2. Description of Related Art Including Information Disclosed Under 37 CFR 1.97 And 1.98

Typically, orthodontic brackets have profiles that cause irritation of the inner lip surfaces of a patient because the bracket is rectangular in cross section and its edges protrude too far above the top of the tooth. Typical orthodontic bracket designs are shown in various U.S. patents such as Wildman et al. (U.S. Pat. No. 5,613,850), Damon (U.S. Pat. No. 5,466,151) and in published application no. U.S.2004/0072117 to Farzin-Nia et al.

BRIEF SUMMARY OF THE INVENTION

A ligating tool comprises a handle section and an end section affixed thereto, the end section having two claws, each claw having an opening with two lobes.

The foregoing and other objectives, features, and advantages of the invention will be more readily understood upon consideration of the following detailed description of the invention, taken in conjunction with the accompanying drawings.

BRIEF DESCRIPTION OF THE SEVERAL VIEWS OF THE DRAWINGS

FIG. 9 is a cutaway side away taken along line 9-9 of FIG. 9 with an archwire shown in dashed outline.

FIG. 10 is a cutaway view taken along line 10-10 of FIG. 8.

FIG. 13 is a perspective view of a ligating tool for use with the disclosed top part.

FIG. 14 is a close up perspective view of the end of a ligating tool showing the detailed shape of the openings.

FIG. 19 is a cross section along line 19-19 in FIG. 18.

FIG. 20 is a cross section along line 20-20 in FIG. 18.

FIG. 21 is a plan view of the positioning jig.

DETAILED DESCRIPTION OF PREFERRED EMBODIMENT

Figure 1:
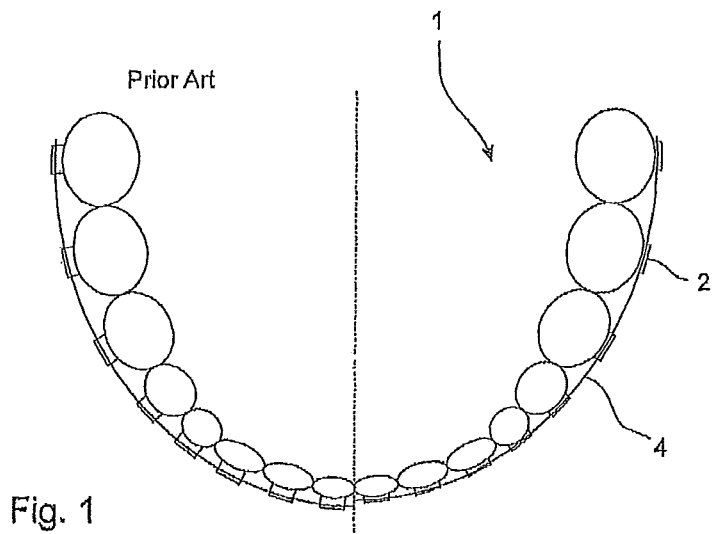
FIG. 1 is a schematic view of a tooth correction means formed of a plurality of tooth top parts and a connecting means.

The invention relates to a tooth top part for a tooth correction means, with a base body at which a tooth support surface is formed for being fixed at a tooth surface by bonding, and which is provided with a guide recess which is formed for receiving a connecting means for coupling neighbouring tooth top parts and which passes through the base body in spaced relationship to the tooth support surface along a guiding axis.

A tooth top part of this type, which is also referred to as a bracket, is known from DE 20 2009 008571 U1. The known tooth top part is formed at an outward-facing surface of a tooth for being fixed by bonding, and to that end comprises a tooth support surface which is used as an adhesive surface for adhesively attaching (adhering) the tooth top part to the surface of the tooth. The tooth top part is provided with a groove-type recess extending along a guiding axis and being spaced from the tooth support surface. The known tooth top part comprises a substantially H-shaped cross section in a cross sectional plane normal to the guiding axis. The recess in the tooth top part permits insertion of a connecting means, which couples tooth top parts attached to neighbouring teeth and permits transmission of forces between the teeth. The forces and, if applicable, the torques transmitted by the connecting means enable the teeth to move relative to each other and permit correction of false positioning (malocclusion) of teeth.

The tooth top part known from the prior art has a drawback that the H-shaped cross section, which may be approximated by a rectangular envelope (curve) in the cross sectional planet causes irritations of the mouth mucous membrane (oral mucosa) in particular at the inside of the lips. This results in reduced wearing comfort for a tooth correction means formed by a plurality of such tooth top parts.

It is an object of the invention to provide a tooth top part which comprises improved adjustment to the anatomical conditions in the mouth region and thus causes less irritation of the mucous membranes.

This object is achieved in a tooth top part as mentioned in the above introduction using the features of claim 1 which provides that the base body comprises a substantially triangular or circular section shaped cross section in a cross sectional plane normal to the guiding axis.

The triangular or circular section shaped cross section guarantees reduced friction during relative movements between the tooth top parts and the opposing mucous membrane. Thus, due to the reduced friction, the mucous membranes will be irritated less both during talking and food intake, and discomfort caused by sore spots in the mucous membrane is reduced. Preferably, compared to known tooth top parts, these tooth top parts have a reduced overall height, which may provide a further reduction in mucous membrane irritations. Preferably, the height of the tooth top part in a direction normal to the tooth surface is less than 2.5 times, in particular less than 2 times, the largest edge length (for instance with a rectangular cross section) or the diameter of the connecting means. More preferably, the connecting means comprises a largest edge length or a diameter selected to be less than 0.5 mm, in particular less than 0.4 mm.

Further advantageous embodiments are presented in the sub-claims.

Appropriately, a base line of the substantially triangular or circular section shaped cross section is formed by the tooth support surface, and a mean perpendicular to the base line comprises a length less than 50 percent of the length of the base line. With this shape of the profile of the tooth top parts, an advantageous ratio is achieved between the size of the tooth support surface required for secure immobilization of the tooth top parts at the tooth surfaces and the height of the respective tooth top part. The length of the mean perpendicular corresponding to the maximum height of the tooth top part beyond the tooth surface is small compared to known tooth top parts. As a result, when combined with the triangular or circular section shaped cross section of the tooth top part, a particularly gentle use of the tooth correction means constituted with the tooth top parts according to the invention can be achieved.

Preferably, each of the outer surfaces of the base body, adjacent to the tooth support surface, include acute angles, preferably less than 45 degrees, more preferably less than 35 degrees, particularly less than 25 degrees, with the tooth support surface. The outer surfaces of the tooth top part are those surfaces at the base body that are in particularly intensive contact with the opposing mucous membranes of the mouth region. The smaller the selected angle between the outer surface and the tooth support surface, the greater the wearing comfort of the tooth correction means constituted by the tooth top parts. However, since reception of the connecting means is always required, the angles cannot be reduced at will.

The triangular cross section of the base body may be formed as an isosceles triangle having identical acute angles between the two outer surfaces and the tooth support surface. Alternatively, the triangular cross section may be formed as a triangle at will where the acute angles included between the respective outer surface and the tooth support surface are selected differently. The circular section shaped cross section may be selected as a symmetrical or asymmetrical circular section.

In a further improvement of the invention, transitional regions between the outer surfaces and/or between an outer surface and the tooth support surface are formed with a rounding-off radius. This avoids sharp edges at the transitions between the outer surfaces or between the outer surface and the tooth support surface which too could give rise to unwanted mucous membrane irritations.

Appropriately, the, preferably undercut, guide recess is formed as a groove-type indentation starting from one of the outer surfaces of the base body. A groove-type indentation enables comfortable and rapid insertion and, if required, removal of the preferably wire-shaped connecting means into the guide recess and from the guide recess, respectively. This is particularly true if the groove opening of the guide recess extends alongside the guiding axis of the guide recess, thus enabling insertion/removal of the connecting means crosswise/transverse to the direction of its overall extension. Preferably, the guide recess is formed with an undercut that, for instance, allows the connecting means to be locked within the guide recess.

Advantageously, at least one, preferably sectionally elastic, snap-on nose is formed at the base body, said snap-on nose regionally limiting the groove-type indentation and being formed for lockingly receiving the connecting means in the guide recess. The snap-on nose is meant to immobilize the connecting means at the tooth top part such that, on one hand, the latter is able to transmit the desired forces between adjacent teeth and, on the other hand, can be easily attached at the tooth top part and, if required, removed again therefrom. Preferably, the snap-on nose is formed as an at least sectionally elastic spring nose enabling snap-in of the connecting means and self-locking, in particular positive locking (form-locking), immobilization of the connecting means at the tooth top part. Alternatively, the groove-type recess may also be closed using a separate locking element or a locking element integrally attached to the base body, wherein the locking element may, for instance, be shifted or swung/pivoted between a locked position and an open position.

In an advantageous improvement of the invention, the snap-on nose is formed for self-locking, in particular positive locking (form-locking), immobilization of the connecting means at the base body. With a self-locking design of the snap-on nose, the connecting means is pushed into the tooth top part while being elastically deformed and, when reaching a predetermined functional position, will be immobilized solely by the resilience (elastic restoration properties) of the snap-on nose without any effort by the user. Preferably, the connecting means, the guide recess in the tooth top part and the snap-on nose are coordinated such that immobilization of the connecting means by positive locking is achieved.

Preferably, the base body is made of a preferably tooth-colored, clear or translucent synthetic material (plastics material). This enables the tooth top parts to be inconspicuously arranged within the mouth region of a patient. More preferably, the tooth top parts are formed in different colorings and/or degrees of transparency in order to allow for low contrast adaptation to the respective tooth color.

Appropriately, the groove-type indentation is formed for lockingly receiving a profiled connecting means which is formed for transmitting torsional forces between neighbouring tooth top parts. This enhances the versatility of the tooth correction means made of the tooth top parts according to the invention by the possibility of inducing pivoting movements between neighbouring teeth. More preferably, the connecting means comprises a square or rectangular cross section which is at least partially mapped in the recess of the tooth top part in order to allow the transmission of torque between the connecting means and the tooth top part.

In an advantageous improvement of the invention, the groove-type indentation is adapted to the connecting means such that a, preferably low friction or nearly zero friction, relative movement of the connecting means with respect to the base body, in particular along/alongside the guiding axis of the recess is enabled. This allows particularly rapid correction of false positioning of teeth without requiring frequent readjustment of the connecting means. The mentioned coordination between the recess and the connecting means is also referred to as self-ligating, since the connecting means is free to move in the recesses of the tooth top parts in accordance with the patient's needs without requiring any additional elements such as rubber rings for immobilizing the connecting means at the tooth top parts.

Preferred embodiments of the invention are shown in the drawings.

In a human tooth arrangement schematically shown in FIG. 1 and comprising molars, canines and incisors, a tooth correction means 1 according to the prior art is shown in the left-hand region of FIG. 1, whereas a tooth correction means according to the invention is shown in the right-hand region of FIG. 1. Both tooth correction means are used in order to achieve a desired arrangement of the teeth with respect to each other. The tooth correction means 1 comprises several tooth top parts which, as an example, are attached at tooth surfaces 3 of all teeth and which are coupled to each other by a connecting means 4 for instance having a wire shape. The connecting means 4 enables the transmission of forces and, if required, also torques between the teeth in order to bring the teeth in a predeterminable position during orthodontic therapy. In the prior art tooth correction means, the tooth top parts clearly extend further from the teeth and the wire thickness of the connecting means is clearly selected to be thicker.

Figure 2:
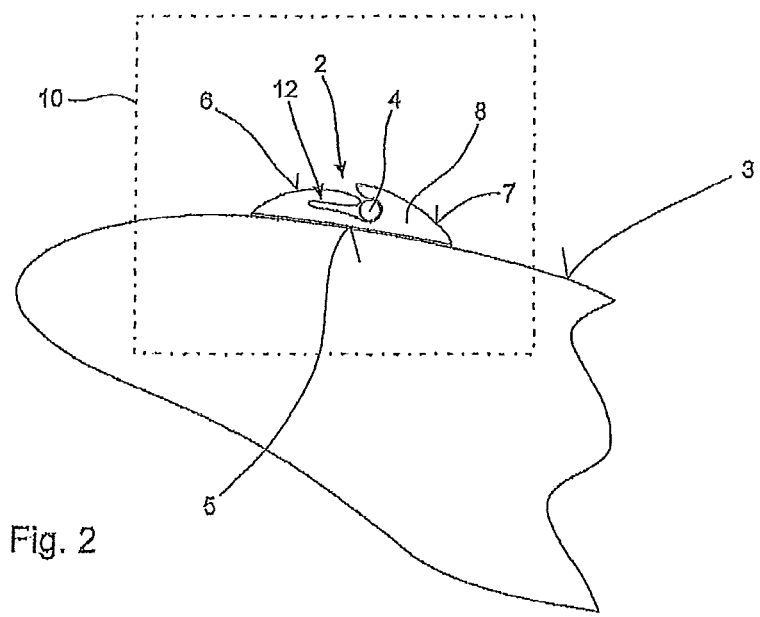
FIG. 2 is a lateral view of a first embodiment of a tooth top part in a functional position.

As can be seen from FIG. 2, the tooth top part 2 according to the invention, which is identical to the base body in the present embodiment, comprises a tooth support surface 5 by means of which it is bonded to the tooth surface 3 in a known manner. The tooth support surface 5 is flanked by a first outer surface 6 and a second outer surface 7 each of which includes an acute angle 18, 19 (FIG. 4) with the tooth support surface 5. Transitional regions between the outer surfaces 6, 7 and the tooth support surface 5 are formed with a rounding-off radii 20, 21.

In the shown embodiment of the tooth top part 2, end faces 8, 9 of the tooth top part 2 are orthogonal to the outer surfaces 6, 7 and to the tooth support surface 5. Thus, the end faces 8, 9 in the shown embodiment of the tooth top part 2 are parallel to a cross-sectional plane identical to the drawing plane of FIGS. 2 and 4.

Figure 4:
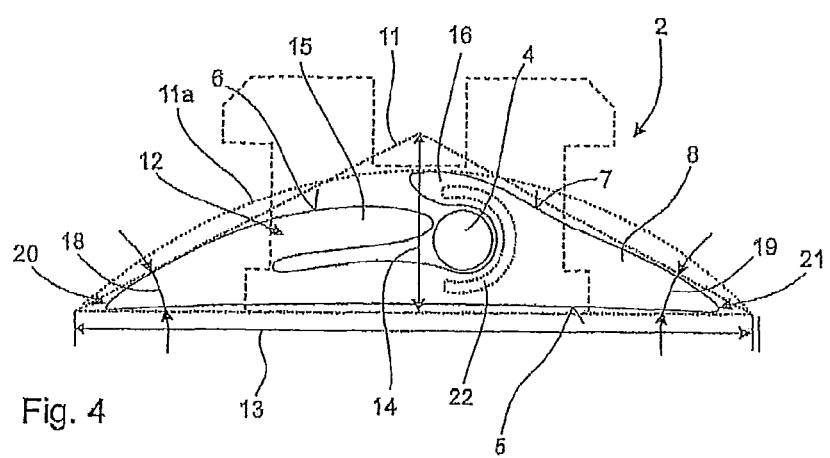
FIG. 4 is a schematic view of the tooth top part according to FIGS. 2 and 3.

As can be seen from the schematic view of FIG. 4, a cross section of the tooth top part 2 is formed such that it is contained within a triangular envelope 11 or within a circular section shaped envelope 11a. A mean perpendicular 14 of the envelope 11 is orthogonal to a base line 13 of the envelope 11, determined by the tooth support surface 5. A length of the mean perpendicular 14 is less than 50 percent, in the present example about 40 percent, of the length of the base line 13, which results in a low profile for the tooth top part 2, thus causing less irritations of the mouth mucous membrane (not shown).

Figure 3:
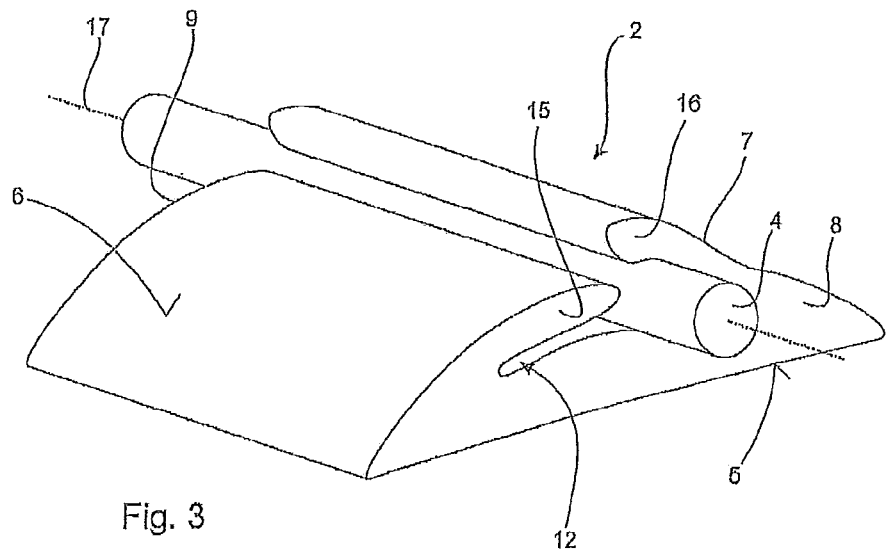
FIG. 3 is a perspective view of the tooth top part according to FIG. 2.

In the embodiment of a tooth top part shown in FIGS. 2 through 4, a recess 12 extending normally to the cross sectional plane 10 is provided with a substantially L-shape profile. For instance, the tooth top part 2 is formed as a geometrically extruded component having a constant cross section normal to the cross sectional plane la throughout its length. Thus, the recess 12 also extends with a constant cross section and thus, determines a guiding axis 17 coinciding with a central axis of the for instance wire-shaped connecting means 4 having a circular cross section.

Due to the substantially L-shaped profile design, a snap-on nose 15 and a snap-on hook 16 for immobilizing/securing the connecting means are formed in the base body 2 of the tooth top part. The snap-on nose 15 is designed for locking the connecting means 4 in the shown functional position within the snap-on hook 16, thus guaranteeing a safe, positive locking (form locking) immobilization of the connecting means 4 at the tooth top part 2 crosswise/transverse to the extension of the connecting means 4. During an assembly operation (not shown), where the connecting means 4 is pushed transversely to its longitudinal extension into the recess 12, both the snap-on nose 15 and the snap-on hook 16 undergo elastic deformation. During the assembly operation, while the snap-on nose 15 is bent toward the tooth support surface 5, the snap-on hook 16 undergoes deformation in the opposite direction. As a result, the recess 12 opens up a cross section enabling insertion of the connecting means 4. As a result of a preferably exclusively elastic deformation of the snap-on nose 15 and the snap-on hook 16, the tooth top part is self-locking for the connecting means 4.

As soon as the connecting means 4 arrives at the functional position shown in FIGS. 2 through 4, the resilience, i.e. elastic restoration forces, of the snap-on nose 15 and the snap-on hook 16 will have a non-positive locking (force locking) and positive locking (form locking) effect for forces occurring within the cross sectional plane la without requiring any additional measures to that end. Both the snap-on nose 15 and the snap-on hook 16 comprise elastic regions formed as solid-state joints enabling elastic pivoting into the assembly position and restoration into the functional position.

In a variant of the tooth top part 2, the snap-on hook 16 may be reinforced using an insert 22, preferably made of an elastic/resilient metal, as shown in FIG. 4.

In the following description of a second embodiment of a tooth top part 22 shown in FIG. 5, components with identical function are given reference numerals increased by 20. The tooth top part 22 is provided for receiving a connecting means 24 having a rectangular cross section in the present case and which enables the transmission of torque between neighbouring tooth top parts 22. The recess 32 is adapted to the connecting means 24 such that the latter engages the snap-on hook 36 via three lateral surfaces and is pressed by the snap-on nose 35 into this region of the recess 32.

Figure 5:
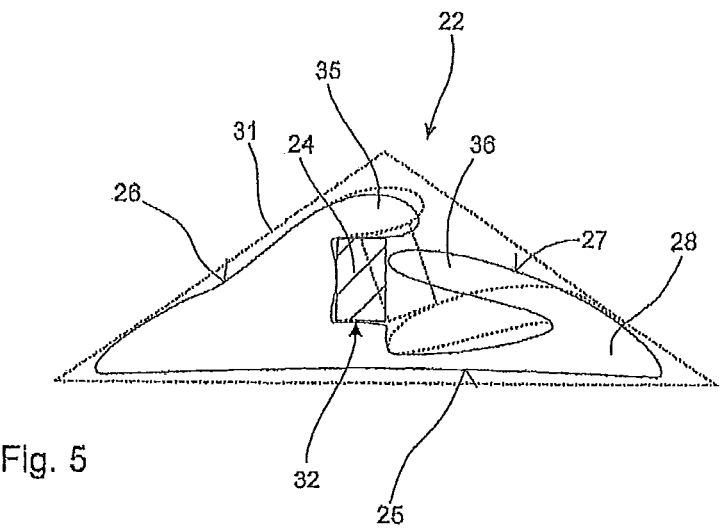
FIG. 5 is a lateral view of a second embodiment of a tooth top part in a functional position shown as solid lines and in an assembly position shown as dotted lines.

As can be seen from the dotted-line representation of FIG. 5, when the connecting means 24 is mounted, the snap-on nose 35 is 10 supposed to be bent downward while the snap-on hook is deformed downward toward the tooth support surface 25. This causes the recess 32 to open up a cross section through which the connecting means 24 can be brought into the functional position, as it exists in the solid-line representation of FIG. 5. After the connecting means 24 has reached the functional position, the snap-on nose 35 and the snap-on hook 36 will pivot back elastically into the initial position shown with solid lines and thus, will cause positive locking (form locking) of the connecting means.

Demounting of the connecting means 24 can be effected by holding down the snap-on nose 35 toward the tooth support surface 25 with a tool (not shown) and subsequently pivoting the connecting means 24 out of the recess 32 by performing a pivoting movement while deforming the snap-on hook 36.

Figure 6:
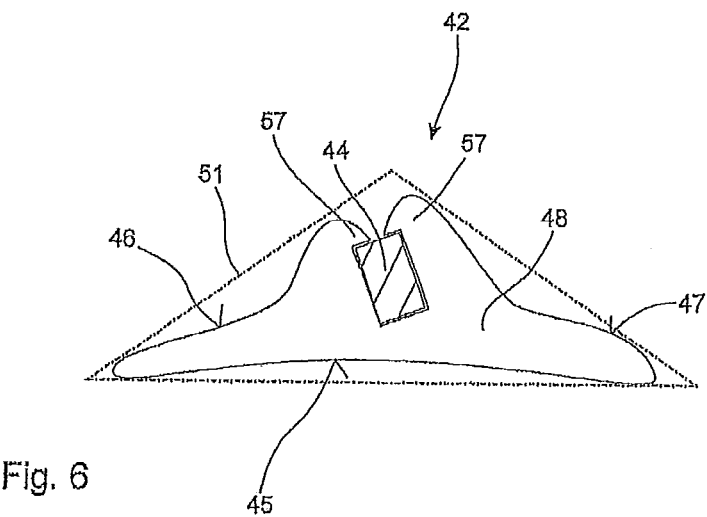
FIG. 6 is a lateral view of a third embodiment of a tooth top part in a functional position.
Figure 7:
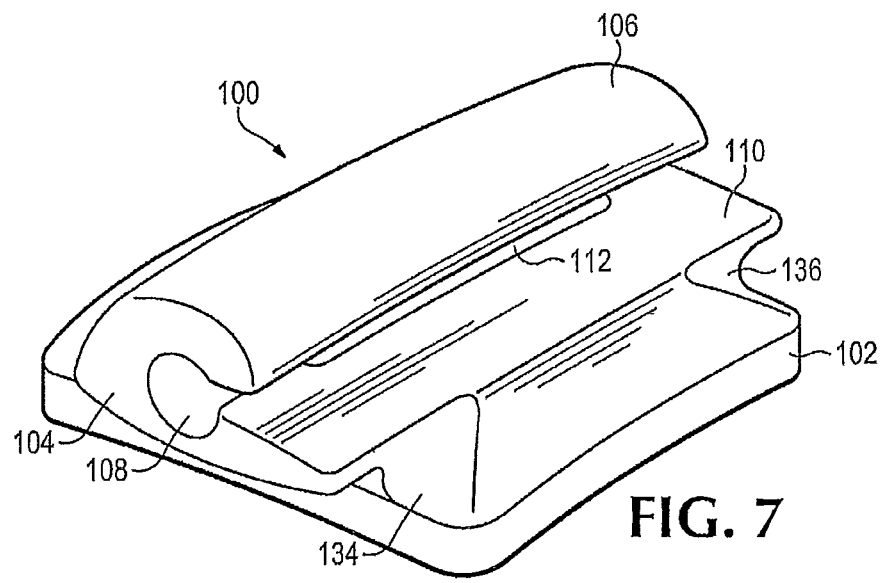
FIG. 7 is a perspective view of another embodiment of a low profile bracket.

A simplified embodiment of a tooth top part 42 is shown in FIG. 6. In this case, the cross section of the recess 52 substantially corresponds to the cross section of the connecting means 44 and is only limited by barbed hooks 57 provided on both sides in the region of the groove opening. These barbed hooks 57 are elastically displaced when the connecting means 44 is inserted into the recess 52, and will move back into the shown position as soon as the connecting means 44 has reached the functional position. The advantage of the embodiment according to FIG. 6 can be considered as having no hollow spaces at the tooth top part 42 due to the corresponding cross sections of the connecting means 44 and the recess 52. Demounting of the connecting means 44 is preferably effected by pulling it out laterally toward the guiding axis oriented normally to the drawing plane of FIG. 6.

The tooth top parts 2, 22, 42 shown in FIGS. 2 through 6 are preferably made of a synthetic material such as a plastics material. Alternatively, the use of ceramics or metal for producing the tooth top parts is possible. In doing so, it may be necessary to modify the geometries of the tooth top parts, in particular in the region of the solid-state joints, in order to guarantee the desired elastic properties. When using synthetic materials such as plastic materials or ceramic materials for the tooth top parts, a regional/sectional reinforcement employing metal inserts may be provided.

The tooth top part 2, 22, 42 according to the invention enables relative displacement and/or pivoting of neighbouring teeth. Given that the tooth top part 2, 22, 42 does not have any hooks and eyelets (no "nooks and crannies"), no additional connecting elements such as rubber bands can be inserted. In order to provide for additional force application to the teeth to be corrected, additional hooks may be provided in the region of the gum line. These additional hooks, which may be attached in a structurally separated manner from the tooth top parts 2, 22, 42 at selected or all teeth and which are preferably made of synthetic material, enable additional connecting elements to be hooked up which are typically significantly shorter than the tooth top parts 2, 22, 42 and, as they are suited exclusively for hooking up additional connecting elements, can be designed in a very skinny fashion. By providing additional hooks in the region of the gum line, these hooks as well can be placed very inconspicuously and in particular at particularly suitable force application points on the teeth to be moved, since this will favor parallel displacement of the teeth. Due to the decoupling of the different force application systems, which are determined by the tooth top parts 2, 22, 42 on one hand and by the additional hooks on the other hand, not only an optically inconspicuous attachment of the corresponding components for the tooth correction means with little irritation of the mouth mucous membrane, but also a particularly efficient movement of the teeth due to the advantageous selectability of the force application points can be achieved.

In another aspect of the invention, a bracket 100 as shown in FIGS. 7-11 includes a base 102 and a top portion 104. The brackets 100 are affixed to teeth 101 (shown in dashed outline). The base 102 has a width in both the gingival-occlusal plane ($L_1$) and a length in the distal-anterior direction ($W_1$). The top portion 104 is made of an elastically deformable hook portion 106 that curls around past the apex to create a substantially cylindrical or tubular archwire channel 108. Note that the interior of this channel could also be rectangular in cross section as shown in the embodiment of FIG. 6. In this embodiment, the snap-on nose is eliminated and a shelf 110 is formed underneath the hook portion 106. The shelf and the distal end of the hook portion 106 form an opening 112 that is slightly smaller than the largest diameter of an archwire 114 (dashed outline in FIG. 9). When the archwire 114 is press fitted into the opening 112, the hook portion 106 elastically deforms allowing the archwire to enter the channel 108. Once the archwire 114 has reached its functional position, the hook snaps back, securing the archwire 114 therein. The archwire may be removed by prying the hook portion 106 upward with a ligating tool 200.

Figure 12:
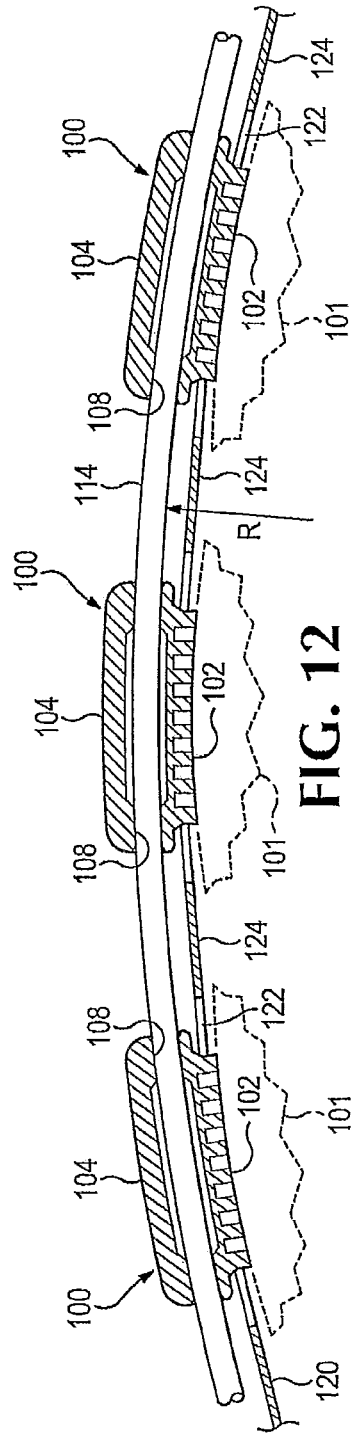
FIG. 12 is a side cutaway view of the brackets of FIG. 11.

The archwire 114 for this bracket is thin. Treatment typically begins with an archwire having a diameter of 0.010". It progresses during the treatment to 0.012" and eventually to 0.014". All archwires fit within the bracket 100, which has a nominal channel diameter of 0.016". As shown in FIG. 12, the archwire channel is larger in the center portion of the bracket for reducing friction.

The archwire has a radius of curvature "R" as also shown in FIG. 12. The interior shape of the hook portion (and hence, of the archwire channel 108) of the top part in the distal-anterior direction is curved and has a radius of curvature made to match the radius of curvature "R" of the archwire. This insures that the archwire slides through the channel with the least amount of friction possible.

Figure 11:
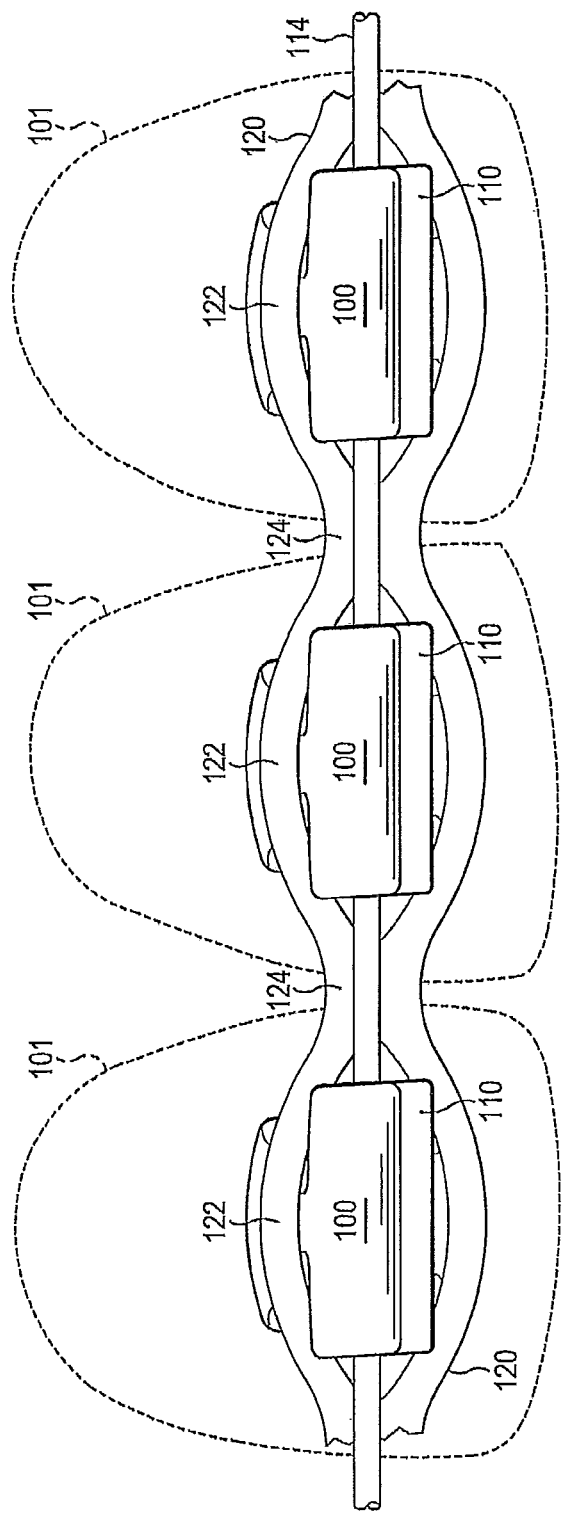
FIG. 11 is a top view of the brackets of FIG. 8 installed on a patient's teeth in dashed outline and connected by a power chain.

The base and the top portion may be configured to provide a tie wing for an elastic power chain 120. An elastic power chain (see FIG. 1) is an elastic band with at least two open loops 122 joined by bridge portions 124. The power chain 120 has three loops and can be looped about adjacent brackets so as to exert a compressive force tending to draw them together as shown in FIG. 11. The power chain may have any number of loops desired.

Figure 8:
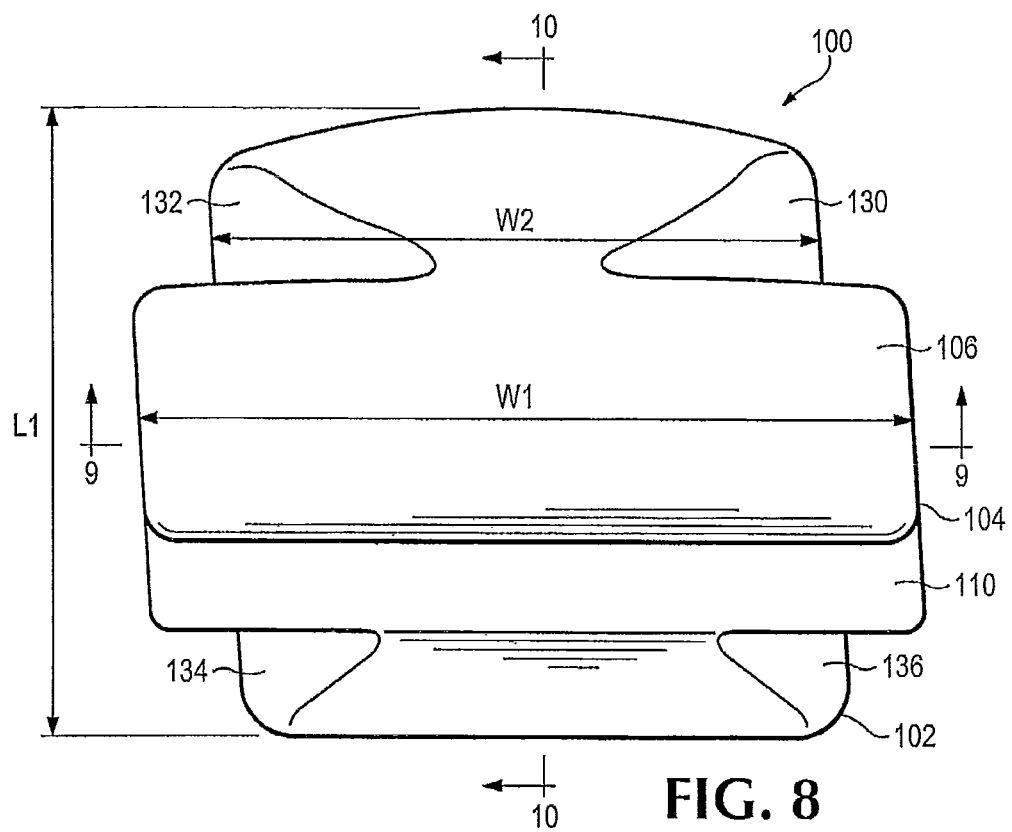
FIG. 8 is a top view of the bracket of FIG. 7.

To form a tie wing, the top portion 104 is made longer in the distal-anterior direction than the width of the base 102 in this same direction as shown in FIG. 8 by the arrows designating W1 and W2. In addition, the base 102 may be chamfered at its corners so that the power chain 120 is retained more easily when it is looped over the top of the bracket. The corners 130, 132, 134 and 136 are all chamfered to provide a surface for retaining the power chain loops 122.

The bracket 100 is a small low-profile bracket in which the mean height "h" is less than half of the length $L_1$ of the base 102 in the gingival-occlusal direction. The low profile insures that the bracket will not irritate the inside of the lips of the patient. Typical dimensions are that the gingival-occlusal length of the base is about 0.135". Thus, the bracket could be 0.140" to 0.130" inches in length. The low profile comes from the height of the bracket, which in a preferred embodiment is about 0.053", but could range, preferably, from about 0.048" to 0.058". The height of the bracket, however, should not exceed half of the gingival-occlusal length. Thus if the length were 0.130", the bracket height should not exceed 0.065". This results in a bracket that is triangular in cross section with a rounded crown at the apex. The triangle is a shallow low-profile shape that makes the bracket comfortable for the patient and is easy to adjust.

Figure 16:
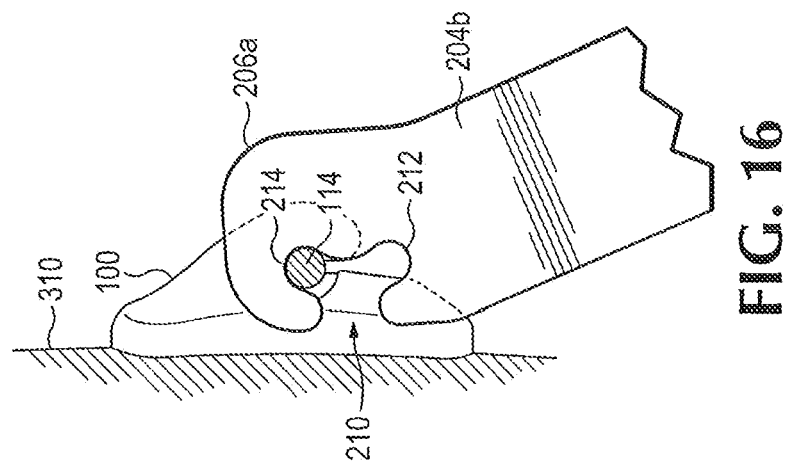
FIG. 16 is a section taken along line 16-16 in FIG. 15.
Figure 15:
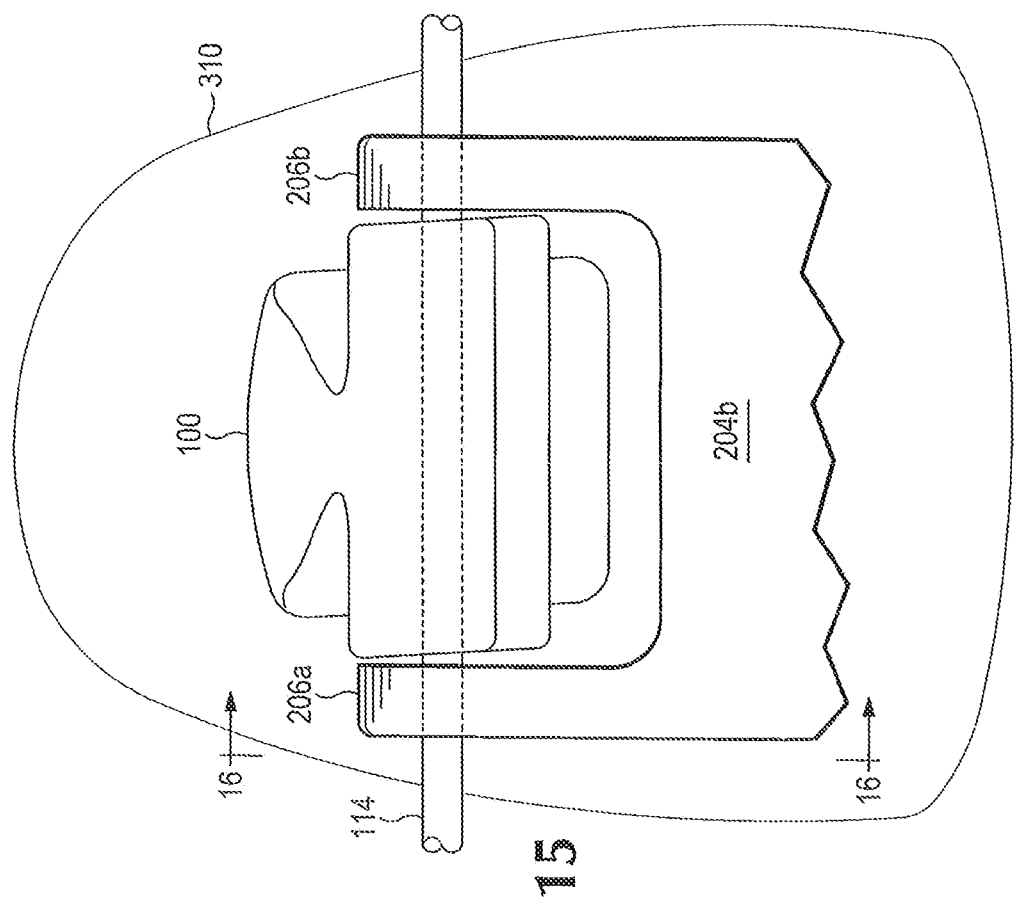
FIG. 15 is a plan view of a ligating tool positioned to remove an archwire from a top part.

Insertion or removal of an archwire 114 to/from the top part 100 is accomplished with a ligating tool 200 designed for the brackets of FIGS. 7-12. As shown in FIG. 13, the tool comprises an elongate handle section 202 which can be held by a user. It may have two end sections 204a and 204b at opposing ends of the handle section 202. The end sections 204a and 204b, best shown in FIG. 14, each comprise a pair of claws 206a and 206b (shown only in connection with end portion 204a) for manipulating the archwire 114. These claws 206a, 206b are spaced apart by a gap 208 to accommodate a bracket top portion 100 between them, as shown in FIG. 15. The gaps 208 on the two end opposed sections 204a and 204b may each be of slightly different width, to accommodate different sized top portions 100. Each claw such as claw 206a has an opening 210, leading to two lobes 212, 214, which form internal pathways, with each lobe being approximately circular and sized so as to releasably engage the archwire 114 in either internal pathway. Given their shape, the lobes are actually hooks that can push or pull the archwire in opposite directions as desired. The lobes 212 and 214 are positioned across from each other on opposite sides of the opening 210 in an opposing relationship to each other. The lower lobe 212, closer to the handle section 202, can push the archwire 114 through the opening 112 into the channel 108. To remove the archwire 114, the upper lobe 214 engages the archwire 114 and, when the tool 200 is rotated around it, pushes it outward and downward, forcing the hook portion 106 upward and pulling the archwire 114 out of the channel 108, as depicted in FIG. 16. Preferably, the end section 204a is placed at an angle to the handle section 202, while the opposite end section 204b is oriented at an angle to the handle section 202 but in the opposite direction so that the tool may be used at a comfortable angle while in the patient's mouth.

Figure 17:
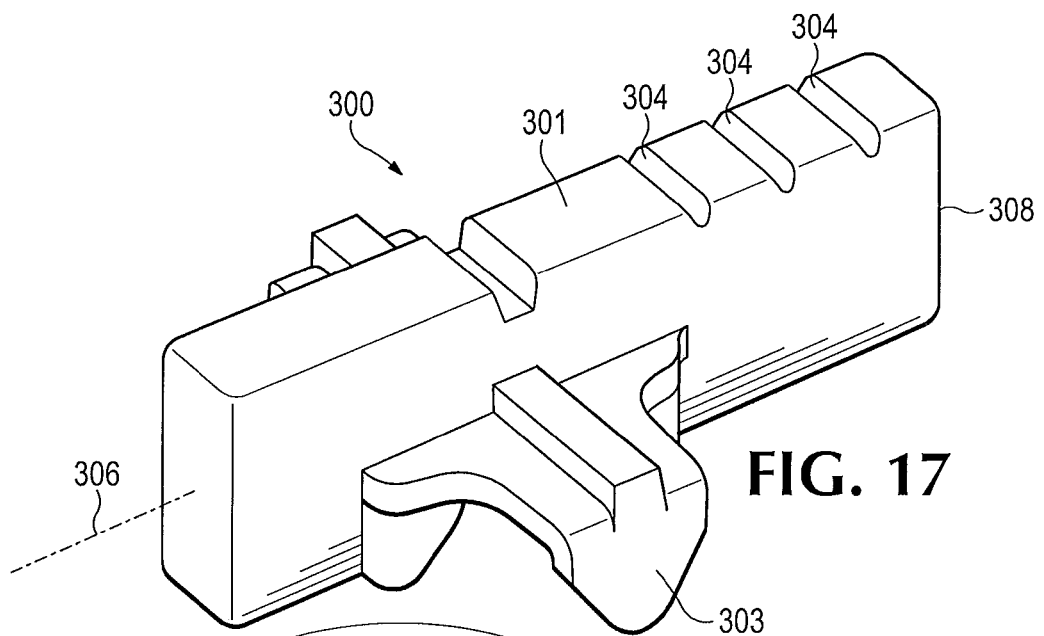
FIG. 17 is a perspective view of a positioning jig for alignment of a top part on a tooth.

To aid in placement of orthodontic appliances such as the top part 100 on a tooth 310, positioning jigs 300, shown in FIG. 17, may be used. Jigs 300 have a cross-like shape with a body 301 and two arms 303. The arms 303 have protrusions 302 which extend slightly into the channel 108 in order to firmly hold the top part 100, as shown in FIG. 20. Because both the jig 300 and the top part 100 are made from elastic materials, the jig 300 may be "snapped" into place and removed by pulling. Jigs 300 are made with notches 304 on the body 301 to assist in positioning of the top part 100 along the path to be traveled by the archwire 114. Each jig 300 is made to be 5 millimeters from the bottom 308 of the jig to the path of the archwire 114. Notches 304 are placed at one millimeter intervals, starting at the bottom, to provide a visual distance reference. Other methods of marking distance, such as paint, are also possible, as are other sizes and intervals. In practice, notches 304 permit a practitioner to adjust the position of each top part 100 visually with reference to the crown of each tooth, to provide the desired path for archwire 114.

Figure 18:
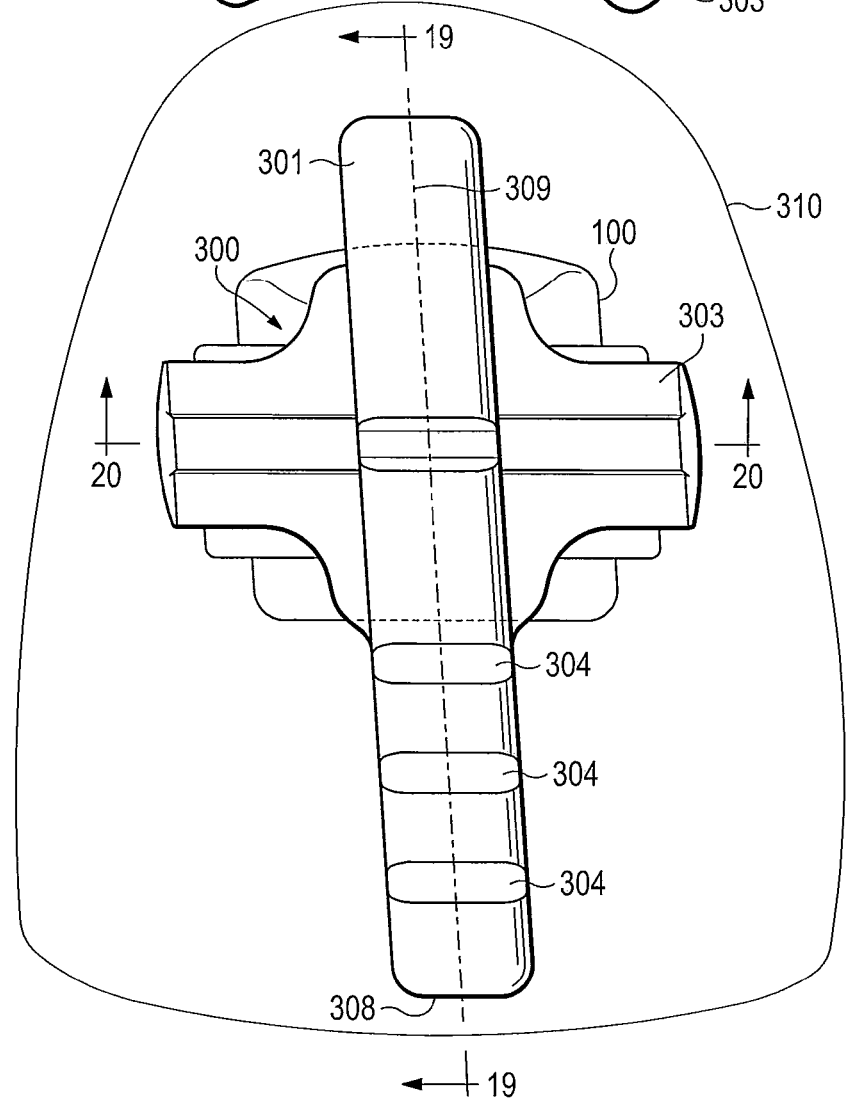
FIG. 18 is a plan view of a positioning jig, attached to a top part, being used to place the top part on a tooth.

Preferably, the jigs 300 are made with different angles 305 formed between the body 301 and the arms 303 of the jig 300. This also aids in visual alignment of the top part 100 on the tooth. When the axis 306 is aligned with the long axis 309 of a tooth 310 as shown in FIG. 18, the channel 108 will be properly positioned to receive the archwire 114. This positioning may result in the application of some torque to the tooth in order to achieve an optimal final result.

The terms and expressions that have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

I claim:

1. In combination, a manipulator tool for inserting an archwire into and removing an archwire from an orthodontic bracket, and an orthodontic bracket comprising:
   a bracket having a predetermined mesial-distal width and a tubular channel for entraining an archwire therein;
   A manipulator tool comprising a handle;
   At least a first end section joined to said handle, said first end section having a pair of claws separated by a first gap exceeding said mesial-distal width, each of said claws having first and second lobes positioned in opposing relationship to each other so as to form openings for receiving said archwire, said lobes forming respective hooks for releasably engaging said archwire to alternately push said archwire into said tubular channel or pull said archwire out of said tubular channel.

2. The manipulator tool of claim 1 wherein said end section is oriented at an angle relative to said handle and extends in a first direction.

3. The manipulator tool of claim 2 further including a second end section at an opposite end of said handle, said end section having a second pair of claws separated by a second gap whose width differs from the width of said first gap.

4. The manipulator tool of claim 3 wherein said second end section is oriented at an angle with respect to said handle and extends in a second direction opposite from the first direction.

* * * * *